United States Patent
Vortman et al.

(10) Patent No.: US 12,409,345 B2
(45) Date of Patent: Sep. 9, 2025

(54) ABERRATION CORRECTIONS FOR DYNAMICALLY CHANGING MEDIA DURING ULTRASOUND THERAPY

(71) Applicant: INSIGHTEC, LTD., Tirat Carmel (IL)

(72) Inventors: Kobi Vortman, Tirat Carmel (IL); Yoav Levy, Hinanit (IL)

(73) Assignee: INSIGHTEC LTD., Tirat Carmel (IL)

( * ) Notice: Subject to any disclaimer, the term of this patent is extended or adjusted under 35 U.S.C. 154(b) by 760 days.

(21) Appl. No.: 17/629,937

(22) PCT Filed: Jul. 24, 2020

(86) PCT No.: PCT/IB2020/000677
§ 371 (c)(1),
(2) Date: Jan. 25, 2022

(87) PCT Pub. No.: WO2021/014221
PCT Pub. Date: Jan. 28, 2021

(65) Prior Publication Data
US 2022/0288424 A1 Sep. 15, 2022

Related U.S. Application Data

(60) Provisional application No. 62/878,481, filed on Jul. 25, 2019.

(51) Int. Cl.
*A61N 7/02* (2006.01)
*A61N 7/00* (2006.01)

(52) U.S. Cl.
CPC ........ *A61N 7/02* (2013.01); *A61N 2007/0039* (2013.01); *A61N 2007/0078* (2013.01); *A61N 2007/0095* (2013.01)

(58) Field of Classification Search
CPC .................. A61N 7/02; A61N 2007/0095
See application file for complete search history.

(56) References Cited

U.S. PATENT DOCUMENTS 11,123,575 B2 9/2021 Vortman et al.
11,358,007 B2 6/2022 De Picciotto et al.
(Continued)

FOREIGN PATENT DOCUMENTS

CN 105682739 A 6/2016
EP 2343103 A1 7/2011
(Continued)

OTHER PUBLICATIONS

Notice for Reason of Rejection for Japanese Patent Application No. 2022-504136, dated Feb. 13, 2023.
(Continued)

*Primary Examiner* — Colin T. Sakamoto
(74) *Attorney, Agent, or Firm* — MORGAN, LEWIS & BOCKIUS LLP

(57) ABSTRACT

Various approaches to delivering ultrasound energy to a target region include, prior to delivery of the ultrasound energy, populating a data structure relating multiple real-time parameter values to corresponding correction values for one or more ultrasound parameter values associated with one or more transducer elements for generating a focal zone of acoustic energy in at least the first portion of the target region; and during the treatment, (i) predicting or causing measurement of at least one of the real-time parameter values in the second portion of the target region or the non-target region; (ii) based at least in part on the predicted or measured real-time parameter value(s) and contents of the data structure, determine the correction value(s) for the ultrasound parameter value(s); and (iii) activate the transducer element(s) based at least in part on the determined correction value(s) for the ultrasound parameter value(s) so as to generate the focal zone in the second portion of the target region.

33 Claims, 10 Drawing Sheets

(56) References Cited

U.S. PATENT DOCUMENTS

| | | | |
|---|---|---|---|
| 2004/0122323 A1* | 6/2004 | Vortman | A61N 7/02 600/459 |
| 2007/0016039 A1* | 1/2007 | Vortman | A61N 7/02 601/2 |
| 2008/0030104 A1 | 2/2008 | Prus | |
| 2008/0221382 A1 | 9/2008 | Karshafian et al. | |
| 2010/0143241 A1 | 6/2010 | Johnson et al. | |
| 2010/0179425 A1* | 7/2010 | Zadicario | A61N 7/02 600/438 |
| 2012/0116221 A1 | 5/2012 | Sehgal et al. | |
| 2013/0046229 A1 | 2/2013 | Konofagou et al. | |
| 2013/0331738 A1 | 12/2013 | Borelli | |
| 2014/0343421 A1 | 11/2014 | Kim et al. | |
| 2014/0378737 A1 | 12/2014 | Carpenter et al. | |
| 2015/0196638 A1 | 7/2015 | Czamola et al. | |
| 2015/0359603 A1* | 12/2015 | Levy | A61N 7/02 703/2 |
| 2018/0071553 A1* | 3/2018 | Vortman | A61N 7/00 |
| 2019/0083065 A1 | 3/2019 | Vitek et al. | |
| 2019/0178851 A1* | 6/2019 | Prus | G01N 29/07 |
| 2019/0350486 A1 | 11/2019 | Walczak et al. | |
| 2020/0085409 A1 | 3/2020 | Grinfeld et al. | |
| 2020/0171327 A1* | 6/2020 | Levy | A61N 5/1048 |
| 2020/0323515 A1 | 10/2020 | Levy | |
| 2021/0146157 A1 | 5/2021 | Levy et al. | |
| 2021/0187331 A1 | 6/2021 | Zadicario et al. | |

FOREIGN PATENT DOCUMENTS

| | | |
|---|---|---|
| EP | 2676702 A1 | 12/2013 |
| JP | 2006-511265 A | 4/2006 |
| JP | 2015-525108 A | 9/2015 |
| JP | 2015-534488 A | 12/2015 |
| WO | WO2010/118307 A1 | 10/2010 |
| WO | WO2013/034709 A1 | 3/2013 |
| WO | WO2014/053950 A1 | 4/2014 |
| WO | WO2014/118632 A1 | 8/2014 |
| WO | WO2018/020315 A1 | 2/2018 |
| WO | WO2018/0130867 A1 | 7/2018 |
| WO | WO2019/0002947 A1 | 1/2019 |
| WO | WO2019/0058171 A1 | 3/2019 |
| WO | WO2019/0116095 A1 | 6/2019 |
| WO | WO2019/0116097 A1 | 6/2019 |
| WO | WO2019/0116107 A1 | 6/2019 |
| WO | WO2021/014221 A1 | 1/2021 |

OTHER PUBLICATIONS

Insightec, Ltd., International Search Report and Written Opinion of the International Searching Authority mailed Nov. 19, 2018 for International Application No. PCT/IB18/000841 (11 pages).
Insightec, Ltd., International Search Report and Written Opinion of the International Searching Authority mailed Nov. 28, 2018 for International Application No. PCT/IB18/000811 (12 pages).
Insightec, Ltd., International Search Report and Written Opinion of the International Searching Authority mailed Nov. 12, 2018 for International Application No. PCT/IB18/000834 (12 pages).
Insightec, Ltd., International Search Report and Written Opinion of the International Searching Authority mailed Nov. 23, 2020 for International Application No. PCT/IB2020/000677 (17 pages).
Insightec, Ltd., Extended European Search Report, EP18180302.4, Nov. 21, 2018, 5 pgs.
Decision to Grant, EP18180302.4, Jan. 30, 2020, 2 pgs.
Decision to Grant, EP18768933.6, Jul. 1, 2021, 3 pgs.
Insightec, Ltd., Communication Pursuant to Article 94(3), EP18759374.4, Sep. 20, 2021, 4 pgs.
Insightec, Ltd., Allowance Notification for Invention, CN201880043567.3, Jan. 30, 2022, 2 pgs.
First Office Action, CN201880056389, Feb. 1, 2021, 19 pgs.
Second Office Action, CN201880056389, Aug. 30, 2021, 19 pgs.
First Office Action, CN201880043399.8, Feb. 2, 2021, 7 pgs.
Notification to Grant Patent Right for Invention, CN201880043399.8, Aug. 30, 2021, 3 pgs.
De Picciotto, Notice of Allowance, U.S. Appl. No. 16/622,004, May 5, 2022, 9 pgs.
Vlacos, F. et al., "Permeability Assessment of the Focused Ultrasound-Induced Blood-Brain Barrier Opening Using Dynamic Contrast-Enhanced MRI," Phys. Med. Biol. 55 (2010) 5451-5466, 16 pages.
Vortman, Office Action, U.S. Appl. No. 15/637,163, May 13, 2019, 15 pgs.
Vortman, Office Action, U.S. Appl. No. 15/637,163, Dec. 6, 2019, 12 pgs.
Vortman, Office Action, U.S. Appl. No. 15/637,163, May 21, 2020, 14 pgs.
Vortman, Final Office Action, U.S. Appl. No. 15/637,163, Sep. 18, 2020, 15 pgs.
Vortman, Notice of Allowance, U.S. Appl. No. 15/637,163, May 28, 2021, 11 pgs.
Levy, Office Action, U.S. Appl. No. 16/622,005, Sep. 29, 2022, 20 pgs.
Jolesz FA. MRI-guided focused ultrasound surgery. Annu Rev Med. 2009;60:417-30. doi: 10.1146/annurev.med.60.041707.170303. PMID: 19630579; PMCID: PMC4005559 (Year: 2009), 17 pgs.
Park et al., Evaluation of permeability, doxorubicin delivery, and drug retention in a rat brain tumor model after ultrasound-induced blood-tumor barrier disruption, Journal of Controlled Release, vol. 250, Mar. 28, 2017, pp. 77-85 (Year: 2017), 9 pgs.
Chai et al., Magnetic-resonance imaging for kinetic analysis of permeability changes during focused ultrasound-induced blood-brain barrier opening and brain drug delivery, Journal of Controlled Release, vol. 192, Oct. 28, 2014, pp. 1-9 (Year: 2014), 9 pgs.

* cited by examiner

| | | TARGET REGION | | | NON-TARGET REGION 1 | | | NON-TARGET REGION 2 | | |
|---|---|---|---|---|---|---|---|---|---|---|
| | | TEMP. $T_1$ | TEMP. $T_2$ | TEMP. $T_3$ | TEMP. $T_1$ | TEMP. $T_2$ | TEMP. $T_3$ | TEMP. $T_1$ | TEMP. $T_2$ | TEMP. $T_3$ |
| TRANSDUCER ELEMENT 1 | FREQ. | | | | | | | | | |
| | AMP. | | | | | | | | | |
| | PHASE | | | | | | | | | |
| | ... | | | | | | | | | |
| TRANSDUCER ELEMENT 2 | FREQ. | | | | | | | | | |
| | AMP. | | | | | | | | | |
| | PHASE | | | | | | | | | |
| | ... | | | | | | | | | |

FIG. 2

| TRANSDUCER ELEMENT | | | | TARGET REGION (PORTION 302) | | | TARGET REGION (PORTION 304) | | |
|---|---|---|---|---|---|---|---|---|---|
| | | | | TEMP. $T_1$ | TEMP. $T_2$ | TEMP. $T_3$ | TEMP. $T_1$ | TEMP. $T_2$ | TEMP. $T_3$ |
| TRANSDUCER ELEMENT 1 | FREQ. | | | | | | | | |
| | AMP. | | | | | | | | |
| | PHASE | | | | | | | | |
| | ... | | | | | | | | |
| TRANSDUCER ELEMENT 2 | FREQ. | | | | | | | | |
| | AMP. | | | | | | | | |
| | PHASE | | | | | | | | |
| | ... | | | | | | | | |

|  | | TARGET REGION | | | NON-TARGET REGION 1 | | |
|---|---|---|---|---|---|---|---|
|  | | TEMP. RANGE $T_1$-$T_2$ | TEMP. RANGE $T_3$-$T_4$ | TEMP. RANGE $T_4$-$T_5$ | TEMP. RANGE $T_1$-$T_2$ | TEMP. RANGE $T_3$-$T_4$ | TEMP. RANGE $T_4$-$T_5$ |
| TRANSDUCER ELEMENT 1 | FREQ. | | | | | | |
|  | AMP. | | | | | | |
|  | PHASE | | | | | | |
|  | ... | | | | | | |
| TRANSDUCER ELEMENT 2 | FREQ. | | | | | | |
|  | AMP. | | | | | | |
|  | PHASE | | | | | | |
|  | ... | | | | | | |

| | | TARGET REGION | | | NON-TARGET REGION 1 | | |
|---|---|---|---|---|---|---|---|
| | | TEMP. RANGE $T_1$-$T_2$ | TEMP. RANGE $T_3$-$T_4$ | TEMP. RANGE $T_4$-$T_5$ | TEMP. RANGE $T_1$-$T_2$ | TEMP. RANGE $T_3$-$T_4$ | TEMP. RANGE $T_4$-$T_5$ |
| TRANSDUCER ELEMENT 1 | FREQ. RANGE $f_1$-$f_2$ | | | | | | |
| | AMP. RANGE $A_1$-$A_2$ | | | | | | |
| | PHASE RANGE $\phi_1$-$\phi_2$ | | | | | | |
| | ... | | | | | | |
| TRANSDUCER ELEMENT 2 | FREQ. RANGE $f_1$-$f_2$ | | | | | | |
| | AMP. RANGE $A_1$-$A_2$ | | | | | | |
| | PHASE RANGE $\phi_1$-$\phi_2$ | | | | | | |
| | ... | | | | | | |

FIG. 3D

ABERRATION CORRECTIONS FOR DYNAMICALLY CHANGING MEDIA DURING ULTRASOUND THERAPY

RELATED APPLICATION

This Application is a United States National Stage Application filed under 35 U.S.C. § 371 of PCT Patent Application Serial No. PCT/IB2020/000677, filed on Jul. 24, 2020, which claims priority to and the benefit of U.S. Provisional Patent Application No. 62/878,481 filed on Jul. 25, 2019. Each of these applications is hereby incorporated by reference in its respective entirety.

FIELD OF THE INVENTION

The present invention relates, in general, to ultrasound therapy, and, in particular, to systems and methods for correcting aberrations resulting from dynamically changing media during the ultrasound therapy.

BACKGROUND

Tissue, such as a benign or malignant tumor, organ, or other body region may be treated invasively by surgically removing the tissue, or with minimal intrusion or fully non-invasively by using, for example, thermal ablation. Both approaches may effectively treat certain localized conditions, but involve delicate procedures to avoid destroying or damaging otherwise healthy tissue.

Thermal ablation, as may be accomplished using focused ultrasound, has particular appeal for treating diseased tissue surrounded by or neighboring healthy tissue or organs because the effects of ultrasound energy can be confined to a well-defined target region. Ultrasonic energy may be focused to a zone having a cross-section of only a few millimeters due to relatively short wavelengths (e.g., as small as 1.5 millimeters (mm) in cross-section at one Megahertz (1 MHz)). Moreover, because acoustic energy generally penetrates well through soft tissues, intervening anatomy often does not impose an obstacle to defining a desired focal zone. Thus, ultrasonic energy may be focused at a small target in order to ablate diseased tissue while minimizing damage to surrounding healthy tissue.

To focus ultrasonic energy at a desired target, drive signals may be sent to an acoustic transducer having a number of transducer elements such that constructive interference occurs at the focal zone. At the target, sufficient acoustic intensity may be delivered to heat tissue until necrosis occurs, i.e., until the tissue is destroyed. Preferably, non-target tissue along the acoustic path through which the acoustic energy passes (the "pass zone") outside the focal zone is exposed to low intensity acoustic beams and thus will be heated only minimally, if at all, thereby minimizing damage to tissue outside the focal zone.

Typically, ultrasonic energy is delivered according to a treatment plan, often based on a predefined model of the target and the patient's anatomy. During treatment, the temperature at the target is monitored using, for example, a magnetic resonance imaging (MRI) apparatus. If the measured temperature is below the desired target temperature for necrosis, the ultrasonic energy transmitted from the transducer is increased. In some situations, however, the temperature at the target is not responsive to the increased ultrasonic energy. For example, the ultrasonic beams passing through the non-target tissue in the pass zone may be defocused due to a change in the properties of the non-target tissue resulting from absorption of ultrasound energy during the ultrasound procedure; thus, increasing the acoustic energy may not significantly increase the intensity of the defocused beam at the target region.

Accordingly, there is a need for an approach that considers the effects of the ultrasonic energy absorbed by the non-target tissue during the ultrasound procedure so as to increase efficiency of the target treatment while avoiding damage to the non-target tissue.

SUMMARY

Various embodiments of the present invention provide systems and methods for taking into account the effects of the ultrasonic energy absorbed or refracted by the non-target tissue during an ultrasound procedure and, based thereon, dynamically adjusting one or more ultrasound parameter values to achieve an additional objective (e.g., optimal focusing, matching of the acoustic coupling, etc.) besides the temperature at the target region. In some embodiments, a data structure such as an autofocusing correction table that relates multiple temperature values to corresponding ultrasound parameter values (e.g., frequencies, amplitudes, phases, etc.) associated with each transducer element and relevant to generating an optimal focus at the target (or other objective) is established prior to and/or during the ultrasound procedure. Additionally or alternatively, in some embodiments, a change in the value of an ultrasound parameter, rather than the value itself, is used. For example, a temperature change in the skull may be related to a change to one or more ultrasound parameter values such as a phase, i.e., the change in the phase aberration depends in a known way on the change in skull temperature. As a result, when the skull temperature rises from a baseline level to new level, the change is predictive of the phase aberration, which may be corrected accordingly by lookup in the autofocusing correction table. Thus, the measured value may be the value of a parameter such as temperature or a change in the parameter value; and the parameter may relate to the target itself or another region (e.g., the skull) that is predictive of effects at the target.

The autofocusing correction table may be established by generating and/or introducing an acoustic reflector (e.g., microbubbles) at the target region and measuring and analyzing reflected signals therefrom. During the ultrasound procedure, based on the established autofocusing table and the temperature measured in real time (e.g., using MRI) and/or predicted using a physical model, the corresponding ultrasound parameter values for generating the optimal focus at the target region can be determined. In some embodiments, a temperature distribution in the target and/or non-target region is measured in real time during the ultrasound procedure; based on the temperature distribution and the geometry of the transducer elements, a specific temperature value (e.g., a temperature increase) in the non-target tissue (e.g., the skull) along the acoustic path from each of the transducer elements to the target region can be determined and associated with the corresponding transducer element. The ultrasound parameter value(s) associated with each transducer element for compensating for the aberrations resulting from the temperature increase along its beam path to the target can then be determined. During treatment, the transducer elements may be activated based on the parameter values determined using the autofocusing table and/or the specific temperature values associated with the transducer elements. In various embodiments, after the optimal focus is generated, the power of at least some of the transducer elements may be increased to elevate the temperature at the target to the desired target temperature for tissue necrosis or other therapeutic effect It should be noted the temperature is only one parameter whose change is predictive of a corresponding change in an ultrasound parameter value such as frequency, amplitude and/or phase (due to change in acoustic properties) and moreover, the measured value need not be at the target even though the target is the region of interest. Other parameters, such as a change in tissue perfusion, the number of cavitation events, the accumulated energy absorbed in the target/non-target region, the number of sonications, a time interval between sonications, the contrast in MRI images, a temperature profile as a function of time, an amplitude and/or a phase of an acoustic signal reflecting from the intervening tissue (e.g., skull) located in the pass zone, etc., are other parameters whose changes may predictably relate to a corresponding change in the ultrasound parameter value (due to change in acoustic properties of the target and/or non-target tissue) and thus are within the scope of the present invention. Accordingly, it should be understood that the data structure described herein may be established by relating values (or changes in the values) of one or more of these parameters to the ultrasound parameter value(s) (or changes therein) associated with each transducer element for generating an optimal focus at the target (or other objective).

Accordingly, various embodiments of the present invention adjust one or more ultrasound parameter values associated with one or more transducer elements to achieve optical focusing or other objective (e.g., matching of the acoustic coupling, etc.) prior to adjusting the ultrasound parameter value(s) for treating the target tissue. In this way, the effects (e.g., defocusing, mismatching of the acoustic coupling, etc.) on the target/non-target tissue resulting from acoustic energy application during the ultrasound procedure can be properly accounted for prior to increasing the temperature at the target. As a result, this approach may generate sufficient acoustic energy and intensity at the focus for treatment purposes while avoiding damage to non-target tissue located in the path zones, thereby advantageously improving both treatment efficiency at the target and safety in non-target tissue regions.

Accordingly, in one aspect, the invention pertains to a system for delivering ultrasound energy to a target region during treatment thereof. In various embodiments, the system includes an ultrasound transducer having multiple transducer elements; and a controller configured to (a) prior to the treatment, populate a data structure relating multiple real-time parameter values to corresponding correction values for one or more ultrasound parameter value(s) (e.g., a frequency, a phase and/or a power level) associated with one or more transducer elements for generating a focal zone of acoustic energy in at least the first portion of the target region; (b) during the treatment, (i) predict or cause measurement of one or more real-time parameter values in the second portion of the target region or the non-target region; (ii) based at least in part on the predicted or measured real-time parameter value(s) and contents of the data structure, determine the correction value(s) for the ultrasound parameter value(s); and (iii) activate the transducer element(s) based at least in part on the determined correction value(s) so as to generate the focal zone in the second portion of the target region. In one implementation, the controller is further configured to repeat steps (i)-(iii) during the treatment.

In some embodiments, each of the real-time parameter values in the data structure represents a change in a value of an associated real-time parameter. The associated real-time parameter may include a temperature, a change in tissue perfusion, a number of cavitation events, an accumulated energy absorbed in the target and/or non-target regions, a number of sonications, a time interval between sonications, a contrast in MRI image, a temperature profile as a function of time, and/or an amplitude and/or a phase associated with an acoustic signal reflected from intervening tissue located between the ultrasound transducer and the target region.

In addition, the data structure may include multiple ranges of the real-time parameter values, each range corresponding to one of the correction value(s) for the ultrasound parameter value(s); the controller may be further configured to identify the range of the real-time parameter values to which the predicted or measured real-time parameter value belongs; and based thereon, determine the correction value for the at least one ultrasound parameter. Alternatively, the data structure may include multiple ranges of the real-time parameter values, each range corresponding to a range of the correction value(s) for the ultrasound parameter value(s); the controller may be further configured to identify the range of the real-time parameter values in the data structure to which the predicted or measured real-time parameter value belongs; based thereon, determine the corresponding range of the correction values; and determine the correction value(s) for the ultrasound parameter value(s) in the range of the correction values based at least in part on where within the identified range the predicted or measured real-time parameter value occurs.

In one embodiment, the system further includes an imager and/or a temperature-measurement device for measuring the real-time parameter value(s) at the second portion of the target region or the non-target region. Additionally or alternatively, the controller may be further configured to predict the real-time parameter value(s) at the second portion of the target region or the non-target region using a physical model. In some embodiments, the controller is further configured to adjust the power level associated with the transducer element(s) so as to achieve a target temperature in the second portion of the target region.

In various embodiments, the real-time parameter values in the data structure do not include the predicted or measured real-time parameter value; the controller is further configured to determine the correction value(s) for the ultrasound parameter value(s) using an interpolation or an extrapolation based on the real-time parameter values and the corresponding correction values for the ultrasound parameter value(s) in the data structure. In addition, the real-time parameter values in the data structure may include combinations of the parameter values measured in real-time and the parameter values computed using a physical model.

The first portion and the second portion of the target region may be the same. Alternatively, the first portion of the target region is different from the second portion of the target region; the controller may then be further configured to determine the correction value(s) for the ultrasound parameter value(s) using an interpolation or an extrapolation based on the real-time parameter values in the data structure and the corresponding correction values for the ultrasound parameter value(s) for generating the focal zone in the first portion of the target region in the data structure.

In some embodiments, the controller is further configured to determine an acoustic energy delivered to the focal zone by the transducer element(s) after traversing an intervening tissue region; and adjust a power level associated with the transducer element(s) based at least in part on the delivered acoustic energy. For example, the controller may be further configured to reduce the power level of the transducer element(s) when the delivered acoustic energy in the focal zone is below a predetermined threshold. Conversely, the controller may be further configured to increase the power level of the transducer element(s) when the delivered acoustic energy in the focal zone exceeds a predetermined threshold. In one embodiment, the controller is further configured to predict or cause measurement of a distribution of the real-time parameter value(s) in the second portion of the target region or the non-target region; the correction value(s) for the parameter value(s) can be further determined based on the predicted or measured distribution of the real-time parameter value(s).

In another aspect, the invention relates to a method of delivering ultrasound energy from an ultrasound transducer having multiple transducer elements to a target region. In various embodiments, the method includes (a) prior to delivery of the ultrasound energy, populating a data structure relating multiple real-time parameter values to corresponding correction values for one or more ultrasound parameter values (a frequency, a phase and/or a power level) associated with one or more transducer elements for generating a focal zone of acoustic energy in at least the first portion of the target region; (b) predicting or causing measurement of one or more real-time parameter values in a second portion of the target region or a non-target region; (c) based at least in part on the predicted or measured real-time parameter value and contents of the data structure, determining the correction value(s) for the ultrasound parameter value(s) associated with the transducer element(s); and (d) activating the transducer element(s) based at least in part on the determined correction value(s) for the ultrasound parameter value(s) so as to generate the focal zone in the second portion of the target region.

In some embodiments, each of the real-time parameter values in the data structure represents a change in a value of an associated real-time parameter. The associated real-time parameter may include a temperature, a change in tissue perfusion, a number of cavitation events, an accumulated energy absorbed in the target and/or non-target regions, a number of sonications, a time interval between sonications, a contrast in MRI image, a temperature profile as a function of time, and/or an amplitude and/or a phase associated with an acoustic signal reflected from intervening tissue located between the ultrasound transducer and the target region.

In addition, the data structure may include multiple ranges of the real-time parameter values, each range corresponding to one of the correction value(s) for the ultrasound parameter value(s); the controller may be further configured to identify the range of the real-time parameter values to which the predicted or measured real-time parameter value belongs; and based thereon, determine the correction value for the at least one ultrasound parameter. Alternatively, the data structure may include multiple ranges of the real-time parameter values, each range corresponding to a range of the correction value(s) for the ultrasound parameter value(s); the controller may be further configured to identify the range of the real-time parameter values in the data structure to which the predicted or measured real-time parameter value belongs; based thereon, determine the corresponding range of the correction values; and determine the correction value(s) for the ultrasound parameter value(s) in the range of the correction values based at least in part on where within the identified range the predicted or measured real-time parameter value occurs.

In one embodiment, the real-time parameter value(s) at the second portion of the target region or the non-target region is predicted using a physical model. In addition, the method may further include repeating steps (b)-(d) during delivery of the ultrasound energy. Further, the method may further include adjusting the power level associated with the transducer element(s) so as to achieve a target temperature in the second portion of the target region.

In some embodiments, the real-time parameter values in the data structure do not include the real-time temperature; the method further includes computationally determining the correction value(s) for the ultrasound parameter value(s) using an interpolation or an extrapolation based on the real-time parameter values and the corresponding correction values for the ultrasound parameter value(s) in the data structure. In one embodiment, the method further includes predicting or causing measurement of a distribution of the real-time parameter value(s) in the second portion of the target region or the non-target region; the correction value(s) for the ultrasound parameter value(s) can be further determined based on the predicted or measured distribution of the real-time parameter value(s).

The first portion and the second portion of the target region may be the same. Alternatively, the first portion of the target region is different from the second portion of the target region; the method may further include computationally determining the correction value(s) for the ultrasound parameter value(s) using an interpolation or an extrapolation based on the real-time parameter values in the data structure and the corresponding correction values for the ultrasound parameter value(s) for generating the focal zone in the first portion of the target region.

As used herein, the term "substantially" means ±10%, and in some embodiments, ±5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

FIGS. 2 and 3B-3D depict exemplary autofocusing correction tables in accordance with various embodiments of the current invention;

FIG. 3A schematically depicts a target region including multiple portions in accordance with various embodiments of the current invention;

DETAILED DESCRIPTION

Figure 1A:
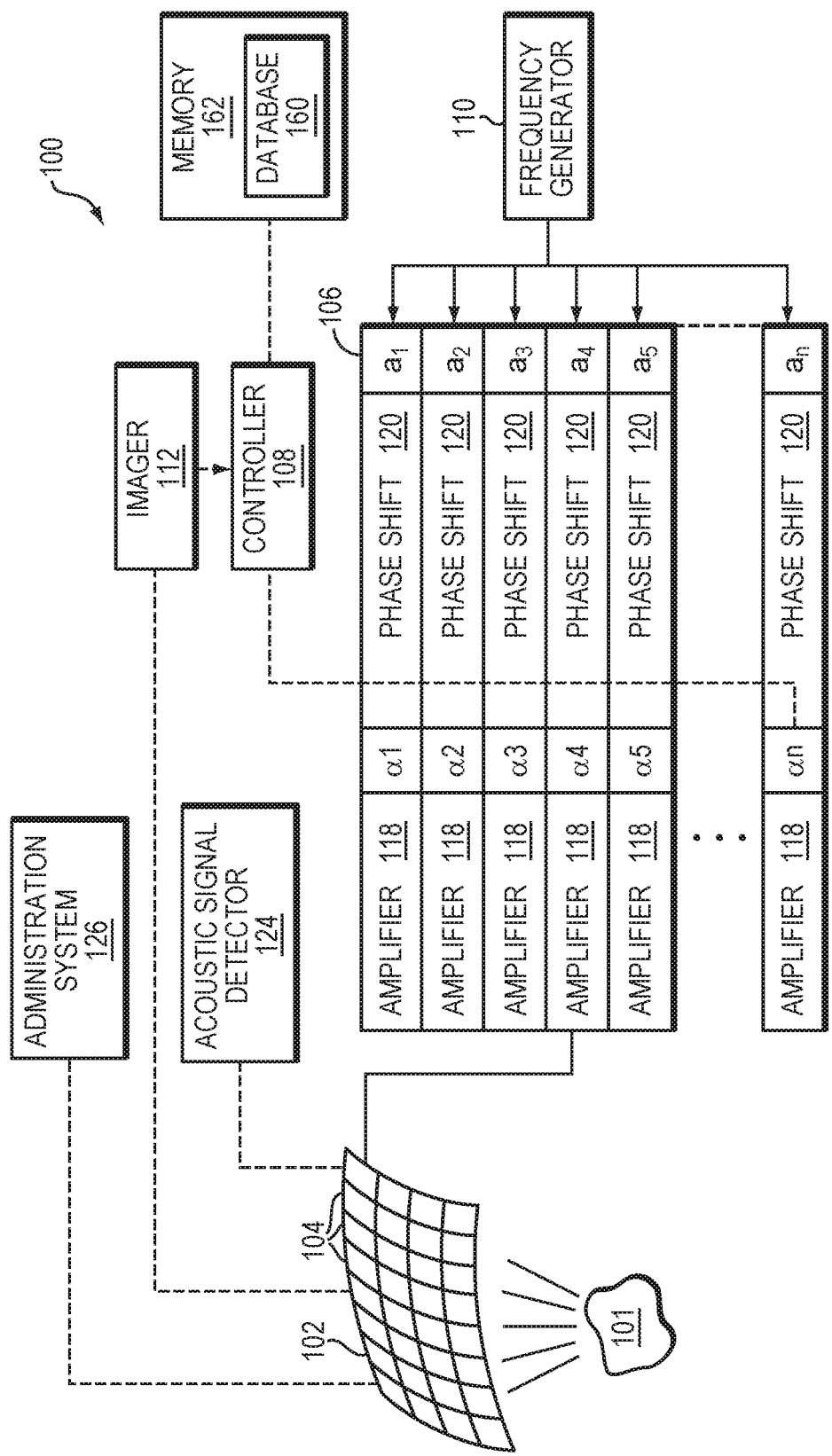
FIG. 1A illustrates a focused ultrasound system in accordance with various embodiments of the current invention.

FIG. 1A illustrates an exemplary ultrasound system 100 for focusing ultrasound onto a target region 101 in a patient. The system 100 can shape the ultrasonic energy in various ways, producing, for example, a point focus, a line focus, a ring-shaped focus, or multiple foci simultaneously. In various embodiments, the system 100 includes a phased array 102 of transducer elements 104, a beamformer 106 driving the phased array 102, a controller 108 in communication with the beamformer 106, and a frequency generator 110 providing an input electronic signal to the beamformer 106.

The array 102 may have a curved (e.g., spherical or parabolic) shape suitable for placing it on the surface of a skull or a body part other than the skull, or may include one or more planar or otherwise shaped sections. Its dimensions may vary, depending on the application, between millimeters and tens of centimeters. The transducer elements 104 of the array 102 may be piezoelectric ceramic, capacitive micromachined ultrasonic transducer (CMUT) or microelectromechanical systems (MEMS) elements, and may be mounted in silicone rubber or any other material suitable for damping the mechanical coupling between the elements 104. Piezo-composite materials, or generally any materials shaped in a manner facilitating conversion of electrical energy to acoustic energy, may also be used. To assure maximum power transfer to the transducer elements 104, the elements 104 may be configured for electrical resonance, matching input impedance.

The transducer array 102 is coupled to the beamformer 106, which drives the individual transducer elements 104 so that they collectively produce a focused ultrasonic beam or field. For n transducer elements, the beamformer 106 may contain n driver circuits, each circuit including or consisting of an amplifier 118 and a phase shift circuit 120; drive circuit drives one of the transducer elements 104. The beamformer 106 receives a radio frequency (RF) input signal, typically in the range from 0.1 MHz to 4.0 MHz, from the frequency generator 110, which may, for example, be a Model DS345 generator available from Stanford Research Systems. The input signal may be split into n channels for the n amplifiers 118 and delay circuits 120 of the beamformer 106. In some embodiments, the frequency generator 110 is integrated with the beamformer 106. The radio frequency generator 110 and the beamformer 106 are configured to drive the individual transducer elements 104 of the transducer array 102 at the same frequency (or in some embodiments, different group of elements at different frequencies), but at different phases and/or different amplitudes.

The amplification or attenuation factors $\alpha_1$-$\alpha_n$ and the phase shifts a1-a, imposed by the beamformer 106 serve to transmit and focus ultrasonic energy through inhomogeneous tissue (e.g., the patient's skull or different tissues located in the acoustic paths of ultrasound beams from the transducer elements to the target region or "path zones") onto the target region (e.g., a region in the patient's brain). Via adjustments of the amplification factors and/or the phase shifts, a desired shape and intensity of a focal zone may be created at the target region.

The amplification factors and phase shifts may be computed using the controller 108, which may provide the relevant computational functions through software, hardware, firmware, hardwiring, or any combination thereof. For example, the controller 108 may utilize a general-purpose or special-purpose digital data processor programmed with software in a conventional manner, and without undue experimentation, to determine the frequency, phase shifts and/or amplification factors of the transducer elements 104. In certain embodiments, the controller computation is based on information about the characteristics (e.g., structure, thickness, density, etc.) of intervening tissues located between the transducer 102 and the target 101 (e.g., the pass zone) and their effects on propagation of acoustic energy. In various embodiments, such information is obtained from an imager 112, such as a magnetic resonance imaging (MRI) device, a computer tomography (CT) device, a positron emission tomography (PET) device, a single-photon emission computed tomography (SPECT) device, or an ultrasonography device. Image acquisition may be three-dimensional (3D) or, alternatively, the imager 112 may provide a set of two-dimensional (2D) images suitable for reconstructing a three-dimensional image of the target region 101 and/or other regions (e.g., the region surrounding the target 101, the region in the pass zone located between the transducer and the target 101, or another target region). Image-manipulation functionality may be implemented in the imager 112, in the controller 108, or in a separate device.

In addition, the ultrasound system 100 and/or imager 112 may be utilized to detect signals from an acoustic reflector (e.g., microbubbles) located at or close to (e.g., within 10 mm of) the target region 101 as further described below. Additionally or alternatively, the system 100 may include an acoustic-signal sensor (such as a hydrophone or suitable alternative) 124 that detects transmitted and/or reflected ultrasound from the acoustic reflector, and which may provide the signals it receives to the controller 108 for further processing as detailed below. In addition, the ultrasound system 100 may include an administration system 126 for parenterally introducing the acoustic reflector into the patient's body. Examples of suitable administration systems are described in PCT Publication No. WO 2019/116095, the entire contents of which are incorporated herein by reference. The imager 112, the acoustic-signal sensor 124, and/or the administration system 126 may be operated using the same controller 108 that governs the transducer operation; alternatively, they may be separately controlled by one or more dedicated controllers intercommunicating with one another.

Figure 1B:
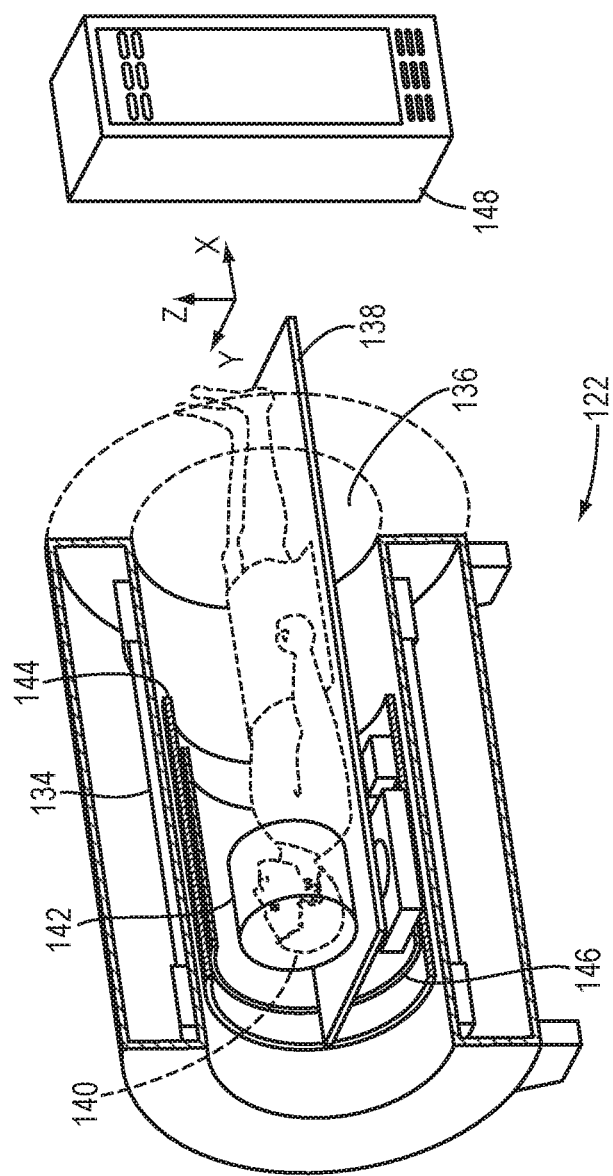
FIG. 1B schematically depicts an exemplary MRI system in accordance with various embodiments of the current invention.

FIG. 1B illustrates an exemplary imager—namely, an MRI apparatus 112. The apparatus 112 may include a cylindrical electromagnet 134, which generates the requisite static magnetic field within a bore 136 of the electromagnet 134. During medical procedures, a patient is placed inside the bore 136 possibly on a movable support table 138. An anatomic region of interest 140 (e.g., the patient's head) may be positioned within an imaging region 142 wherein the electromagnet 134 generates a substantially homogeneous field. A set of cylindrical magnetic field gradient coils 144 may also be provided within the bore 136 and surrounding the patient. The gradient coils 144 generate magnetic field gradients of predetermined magnitudes, at predetermined times, and in three mutually orthogonal directions. With the field gradients, different spatial locations can be associated with different precession frequencies, thereby giving an MR image its spatial resolution. An RF transmitter coil 146 surrounding the imaging region 142 emits RF pulses into the imaging region 142 to cause the patient's tissues to emit magnetic-resonance (MR) response signals. Raw MR response signals are sensed by the RF coil 146 and passed to an MR controller 148 that then computes an MR image, which may be displayed to the user. Alternatively, separate MR transmitter and receiver coils may be used. Images acquired using the MRI apparatus 112 may provide radiologists and physicians with a visual contrast between different tissues and detailed internal views of a patient's anatomy that cannot be visualized with conventional x-ray technology.

The MRI controller 148 may control the pulse sequence, i.e., the relative timing and strengths of the magnetic field gradients and the RF excitation pulses and response detection periods. The MRI controller 148 may be combined with the transducer controller 108 into an integrated system control facility.

The MR response signals are amplified, conditioned, and digitized into raw data using a conventional image-processing system, and further transformed into arrays of image data by methods known to those of ordinary skill in the art. The image-processing system may be part of the MRI controller 148, or may be a separate device (e.g., a general-purpose computer containing image-processing software) in communication with the MRI controller 148 and/or the transducer controller 108. Because the response signal is tissue- and temperature-dependent, it can be processed to identify the treatment target region (e.g., a tumor to be destroyed by heat) 101 in the image, as well as to compute a temperature map from the image. Further, the acoustic field resulting from ultrasound application may be monitored in real time, using, e.g., thermal MRI or MR-based acoustic radiation force imaging. Thus, using MRI data, the ultrasound transducer 102 may be driven so as to focus ultrasound into (or near) the target region 101, while the temperature of the target and surrounding tissues and/or the acoustic field intensity are being monitored.

As described above, MR imaging can provide a non-invasive means of quantitatively monitoring in vivo temperatures. This is particularly useful in MR-guided thermal therapy (e.g., MR-guided focused ultrasound (MRgFUS) treatment), where the temperature of the target region 101 should be continuously monitored in order to assess the progress of treatment and to correct for local differences in heat conduction and energy absorption, thereby avoiding damage to tissues surrounding the target. Monitoring (e.g., measurement and/or mapping) of the temperature is generally based on MR imaging (referred to as MR thermometry or MR thermal imaging) in conjunction with suitable image-processing software.

Among various methods available for MR thermometry, the PRF shift method is often the method of choice due to its linearity with respect to temperature change, near-independence from tissue type, and the high spatial and temporal resolution of temperature maps obtained therewith. The PRF shift method is based on the phenomenon that the MR resonance frequency of protons in water molecules changes linearly with temperature (with a constant of proportionality that, advantageously, is relatively constant among tissue types). Since the frequency change with temperature is small, only −0.01 ppm/° C. for bulk water and approximately −0.0096 to −0.013 ppm/° C. in tissue, the PRF shift is typically detected with a phase-sensitive imaging method in which the imaging is performed twice: first to acquire a baseline PRF phase image prior to a temperature change and then to acquire a second phase image after the temperature change—i.e., a treatment image—thereby capturing a small phase change that is proportional to the change in temperature. A map of temperature changes may then be computed from the (reconstructed, i.e., real-space) images by determining, on a pixel-by-pixel basis, phase differences between the baseline image and the treatment image, and converting the phase differences into temperature differences based on the PRF temperature dependence while taking into account imaging parameters such as the strength of the static magnetic field and echo time (TE) (e.g., of a gradient-recalled echo).

In various embodiments, prior to an ultrasound treatment procedure, the MRI apparatus 112 acquires one or more images of the target 101 and/or non-target regions (e.g., regions located in the pass zone between the transducer 104 and the target 101). The acquired MR images provide accurate locational information for the purpose of treatment planning, as well as baseline phase maps for determining the temperature at the target and/or non-target regions. In general, the MRI thermometry sequence starts with acquisition of baseline images (e.g., at the start of the sonication); a new phase image may be acquired every 2 to 5 seconds.

In some embodiments, the ultrasound treatment involves an acoustic reflector (e.g., microbubbles). For example, microbubbles may be generated by acoustic energy (e.g., using the transducer 102) and/or introduced by systemic injection (e.g., using the administration system 126) for autofocusing. Ultrasound waves transmitted from all (or at least some) transducer elements 104 are reflected by the reflector; the reflection signals may be detected by the acoustic-signal sensor 124 and/or the transducer elements 104. The measured signals may then be provided to the controller 108 to obtain information, such as the amplitudes and/or phases, associated with the reflections; these may be compared to the amplitudes and/or phases associated with the transmitted ultrasound waves from the transducer elements 104. Based on the deviations therebetween, the drive signals of the transducer elements 104 may be adjusted so as to compensate for the deviations, thereby improving the focusing properties. In some embodiments, this autofocusing procedure is iteratively performed until optimal focusing properties are achieved. Approaches for autofocusing an ultrasound beam at the target region are provided, for example, in PCT Publication No. WO 2018/020315 and PCT Application No. PCT/M2019/001340 (filed on Dec. 18, 2019); approaches to generating the microbubbles and/or introducing the microbubbles to the target region 101 are provided, for example, in PCT Publication Nos. WO 2018/020315, WO 2019/116107, WO 2019/058171, WO 2019/116097, WO 2019/002947, and WO 2019/116095, and U.S. Patent Publication Nos. 2019/0083065 and 2019/0178851. The entire contents of the foregoing applications are incorporated herein by reference.

In various embodiments, prior to generating a focus with a desired therapeutic temperature at the target region 101 for treatment, the ultrasound parameter value(s) of the transducer 102 are dynamically adjusted so as to achieve an additional objective (e.g., optimal focusing, matching of the acoustic coupling, etc.) at the target region. Referring to FIG. 2, to create an optimal focus at the target 101, in one embodiment, an autofocusing correction table 202 relating the temperatures 204 to one or more corresponding ultrasound parameter values (e.g., a frequency, a power level, a phase, etc.) 206 associated with each transducer element 104 is established prior to the ultrasound treatment procedure. Additionally or alternatively, in some embodiments, the value of at least one ultrasound parameter value is determined based on a change to another parameter (e.g., temperature) rather than the parameter's value itself. For example, a patient-specific 3D skull replica (or an ex-vivo skull) that represents the skull of a patient receiving the ultrasound treatment may be created prior to the ultrasound procedure. The 3D skull replica may then be situated in an environment similar to that used to treat the patient; the ultrasound wave may be applied to the microbubbles introduced/generated at the target region 101, traversing the 3D skull replica.

Based on the measured reflection signals from the target region 101, the ultrasound parameter value(s) (e.g., the power level, phase, frequency, etc.) associated with each transducer element for generating an optimal focus at the target can be determined. In addition, during the pre-treatment ultrasound procedure, the MRI apparatus may be activated to measure the temperature at the target region 101 and/or non-target region (e.g., the skull replica portion located in the pass zone or outside the pass zone). Thus, it is possible to generate the autofocusing correction table 202 by analyzing the reflection signals from the target 101 using the acoustic-signal sensor 124 and/or the transducer elements 104 and measuring the temperature at the target and/or non-target region using the MRI apparatus during the pre-treatment ultrasound procedure; again, the autofocusing correction table 202 relates the temperatures at the target/non-target region to the corresponding ultrasound parameter value(s) associated with each transducer element for generating an optimal focus at the target 101. Approaches to creating the patient-specific 3D skull replica are provided, for example, in U.S. Patent Publication No. 2020/0085409, the entire contents of which are incorporated herein by reference.

In some embodiments, the autofocusing correction table 202 may be created based on a retrospective study of the patients who have previously experienced ultrasound treatment. Additionally and/or alternatively, the autofocusing correction table 202 may be established based on computational prediction using a physical model. For example, the physical model may predict the beam path from each of the transducer elements 104 to the target location 101 based on information about the geometry of the individual transducer elements 104 and their locations and orientations relative to the target 101; this information, in one implementation, is acquired using the imager 112. In addition, the imager 112 may acquire information such as anatomic characteristics (e.g., type, property, structure, thickness, density, etc.) about the target and/or non-target tissue. Based on the acquired information, a tissue model may be created to characterize the material characteristics (e.g., energy absorption of the tissue at the employed frequency or the speed of sound) of the target and/or non-target tissue. Approaches to creating the tissue model are described, for example, in PCT Publication No. WO 2018/130867, the entire disclosure of which is incorporated herein by reference. In some embodiments, the physical model then includes the anatomic and/or material characteristics of the patient's skull along the beam path from each transducer element 104 to the target 101 for predicting the aberrations resulting therefrom. Based on the predicted aberrations, the ultrasound parameter value(s) associated with each transducer element 104 for compensating for the aberrations and thereby creating an optimal focus at the target 101 may be determined.

In addition, the physical model may predict the temperature distribution at the target/non-target regions resulting from the applied ultrasonic energy. For example, based on the relative phase and/or amplitude settings of the ultrasound transducer elements 104 and the anatomic and/or material characteristics of the target/non-target tissue, the physical model may computationally predict the amount of ultrasound energy delivered to the target region and/or non-target regions at a specific ultrasound frequency, the conversion of ultrasound energy or pressure into heat and/or tissue displacement at the target region and/or non-target regions, and/or the propagation of the induced heat and displacement effects through the tissue. Typically, the simulation takes the form of (or includes) differential equations. For example, the physical model may consist of or include the Pennes model and a bioheat equation to simulate heat transfer in tissue. Approaches to simulating the sonications and their effects on the tissue are provided, for example, in U.S. Patent Publication No. 2015/0359603, the entire disclosure of which is hereby incorporated by reference.

In various embodiments, the autofocusing correction table 202 is established during the ultrasound treatment procedure based on (i) computational prediction using the physical model, (ii) the real-time measurements of the temperature at the target/non-target regions (iii) the ultrasound parameter value(s) for creating an optimal focus at the target 101 and (iv) the reflection signals from the target 101. For example, at the beginning of the ultrasound treatment procedure when the temperatures at the target/non-target regions are below a threshold (e.g., without causing a significant clinical effect), the real-time temperatures of the target and/or non-target tissue may be measured (e.g., using the imager 112), and the corresponding ultrasound parameter value(s) associated with each transducer element 104 for creating an optimal focus at the target 101 may be determined using the autofocusing approach described above. This information and the anatomic and/or material characteristics of the target/non-target tissue (acquired using, for example, the imager 112) may then be provided to the physical model. Based thereon, the physical model may predict or estimate a relationship between the temperatures and the corresponding ultrasound parameter values associated with each transducer element 104 for generating an optimal focus at the target 101. In addition, based on the predicted relationship, the physical model may estimate the ultrasound parameter values for generating the optimal focus in the target region at various temperatures exceeding the threshold in a later stage of the ultrasound treatment procedure. Thus, the autofocusing correction table 202 including the temperatures below and exceeding the threshold and their corresponding ultrasound parameter values can be established. As used herein, the term "significant clinical effect" means having an undesired (and sometimes the lack of a desired) effect that is considered significant by clinicians, e.g., the onset of damage to tissue or other clinically adverse effect, whether temporary or permanent.

Referring again to FIG. 1A, the autofocusing correction table 202 including the temperatures at the target/non-target regions and their corresponding ultrasound parameter values may be stored along with their respective transducer elements 104 in a database 160 in memory 162 accessible by the controller 108. The memory may include or consist essentially of one or more volatile or non-volatile storage devices, e.g., random-access memory (RAM) devices such as DRAM, SRAM, etc., read-only memory (ROM) devices, magnetic disks, optical disks, flash memory devices, and/or other solid-state memory devices. All or a portion of the memory may be located remotely from the ultrasound system 100 and/or the imager 112, e.g., as one or more storage devices connected to ultrasound system 100 and/or the imager 112 via a network (e.g., Ethernet, WiFi, a cellular telephone network, the Internet, or any local- or wide-area network or combination of networks capable of supporting data transfer and communication). As utilized herein, the term "storage" broadly connotes any form of digital storage, e.g., optical storage, magnetic storage, semiconductor storage, etc.

During the ultrasound treatment procedure, the temperature at the target and/or non-target regions may be measured in real-time (e.g., using MRI or other temperature-measurement devices) or predicted using the physical model as described above. Based on the measured/predicted real-time temperature and the established autofocusing table 202, the corresponding ultrasound parameter value(s) associated with each transducer element 104 for generating an optimal focus at the target can be determined. For example, referring again to FIG. 2, if the measured/predicted real-time temperature in the target 101 at time $t_1$ is $T_1$, the ultrasound parameter value(s) associated with the target temperature of $T_1$ in the autofocusing table 202 will be retrieved. The controller 108 may then operate the transducer elements 104 based on the retrieved ultrasound parameter value(s). Optionally, after the optimal focus is generated, the power/intensity of the transducer elements 104 may be increased in order to increase the temperature at the target region 101 to the desired therapeutic temperature.

In various embodiment, increasing the power/intensity of the transducer elements 104 causes additional ultrasound energy to be applied to (and absorbed by) the non-target tissue located in the pass zone; as a result, the ultrasound beam may, again, be defocused. Accordingly, in one implementation, the temperature at the target and/or non-target regions is continuously measured or predicted in real-time, and based on the measured/predicted real-time temperature and the autofocusing correction table 202, the ultrasound parameter value(s) can be dynamically adjusted so as to maintain an optimal focus at the target 101. Such adjustments can be continuously performed until the desired therapeutic temperature is achieved at the target region 101.

In some embodiments, the autofocusing table 202 may not include information corresponding to the real-time measured temperature, T. For example, referring to FIG. 2, the autofocusing table 202 may include the ultrasound parameter values associated with temperatures $T_1$, $T_2$ and $T_3$ only, but $T_1 < T < T_2$. In various embodiments, an interpolation or extrapolation can be performed to acquire the ultrasound parameter value(s) associated with T based on the ultrasound parameter value(s) associated with $T_1$ and $T_2$.

Figures 3A, 3B:
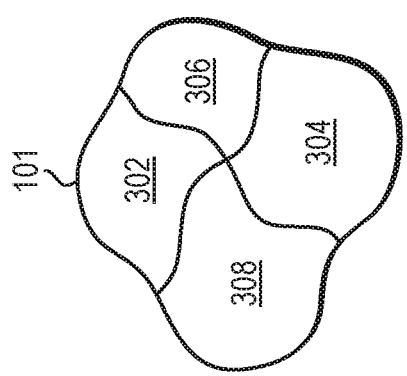

In addition, referring to FIGS. 3A and 3B, the target 101 may span a large volume, and the autofocusing table 202 may include information for generating optimal foci in multiple portions 302, 304 of the target. In this case, an interpolation and/or extrapolation can also be performed to acquire the ultrasound parameter values for generating optimal foci at the target portions 306, 308 that are not included in the autofocusing table 202.

Referring to FIG. 3C, in various embodiments, the autofocusing correction table 202 includes one or more ranges 312 of the temperatures, each range corresponding to one or more of the ultrasound parameter values for generating an optimal focus at the target (or other objective). During treatment, after the real-time temperature is measured (e.g., using MM) and/or predicted (using the physical model), the range of the temperature to which the predicted/measured real-time parameter value belongs can be identified. Based thereon, the ultrasound parameter value(s) corresponding to the identified temperature range for generating the optimal focus at the target can be determined. Alternatively, referring to FIG. 3D, each range 312 of the temperatures may correspond to a range 314 of the ultrasound parameter values for generating an optimal focus at the target (or other objective). Again, upon the real-time temperature being measured/predicted, the range of the temperature to which the predicted/measured real-time parameter value belongs can be identified. Based thereon, the corresponding range 314 of the ultrasound parameter values can be determined. In one embodiment, the ultrasound parameter value(s) within the range 314 for generating the optimal focus at the target can be computed using interpolation or extrapolation. That is, where within the range 312 the measured/predicted temperature falls may linearly determine the appropriate parameter value within the corresponding parameter-value range 314; if the measured/predicted temperature is at the midpoint of one of the ranges 312, for example, the corresponding parameter value may be the midpoint of the corresponding range 314.

In some embodiments, a temperature distribution in the target and/or non-target region is measured in real time (e.g., using MRI) and/or predicted (using the physical model) during the ultrasound procedure; based on the temperature distribution and the geometry of the transducer elements, a specific temperature value (e.g., a temperature increase) in the non-target tissue (e.g., the skull) along the acoustic path from each of the transducer elements 104 to the target region can be determined and associated with the corresponding transducer element 104. The ultrasound parameter value(s) associated with each transducer element 104 for compensating for the aberrations resulting from the temperature increase along its beam path to the target can then be determined. During treatment, the transducer elements 104 may be activated based on the parameter values determined using the autofocusing table and/or the specific temperature values associated therewith.

Further, the intensities of individual transducer elements may be the same or different. In one embodiment, the transducer elements 104 are driven to generate ultrasound energy at their respective intensities while ensuring that the total amount of ultrasound energy delivered to the target 101 collectively satisfies a threshold so as to cause necrosis of the target tissue. The intensity corresponding to each transducer element 104 may be determined based on, for example, the acoustic energy contributed by the transducer element 104 after traversing the pass zone to reach the focus, different thermal sensitivities of tissues in the pass zones, etc. When the energy contribution is below a predetermined threshold, a larger amount of the acoustic energy transmitted from the transducer element is absorbed by the non-target tissue located in the pass zone before reaching the focus; thus, to avoid overheating and damaging the non-target tissue, the transducer element 104 having a lower energy contribution at the focus may be driven to produce a lower-intensity output or, in some embodiments, deactivated during the ultrasound treatment procedure. In contrast, when the energy contribution from the transducer element 104 exceeds the predetermined threshold, the transducer element 104 may be driven to produce a higher-intensity output. This approach may advantageously generate sufficient acoustic energy and intensity in the focus for treatment purposes while avoiding damage to non-target tissue located in the path zones associated with the lower-energy transducer elements. Approaches for determining the energy contribution by each of the transducer elements and controlling the intensities of individual transducer elements based on the energy contributions thereof are provided, for example, in U.S. Patent Publication Nos. 2010/0179425 and 2018/0071553, the entire contents of which are incorporated herein by reference.

Figure 4A:
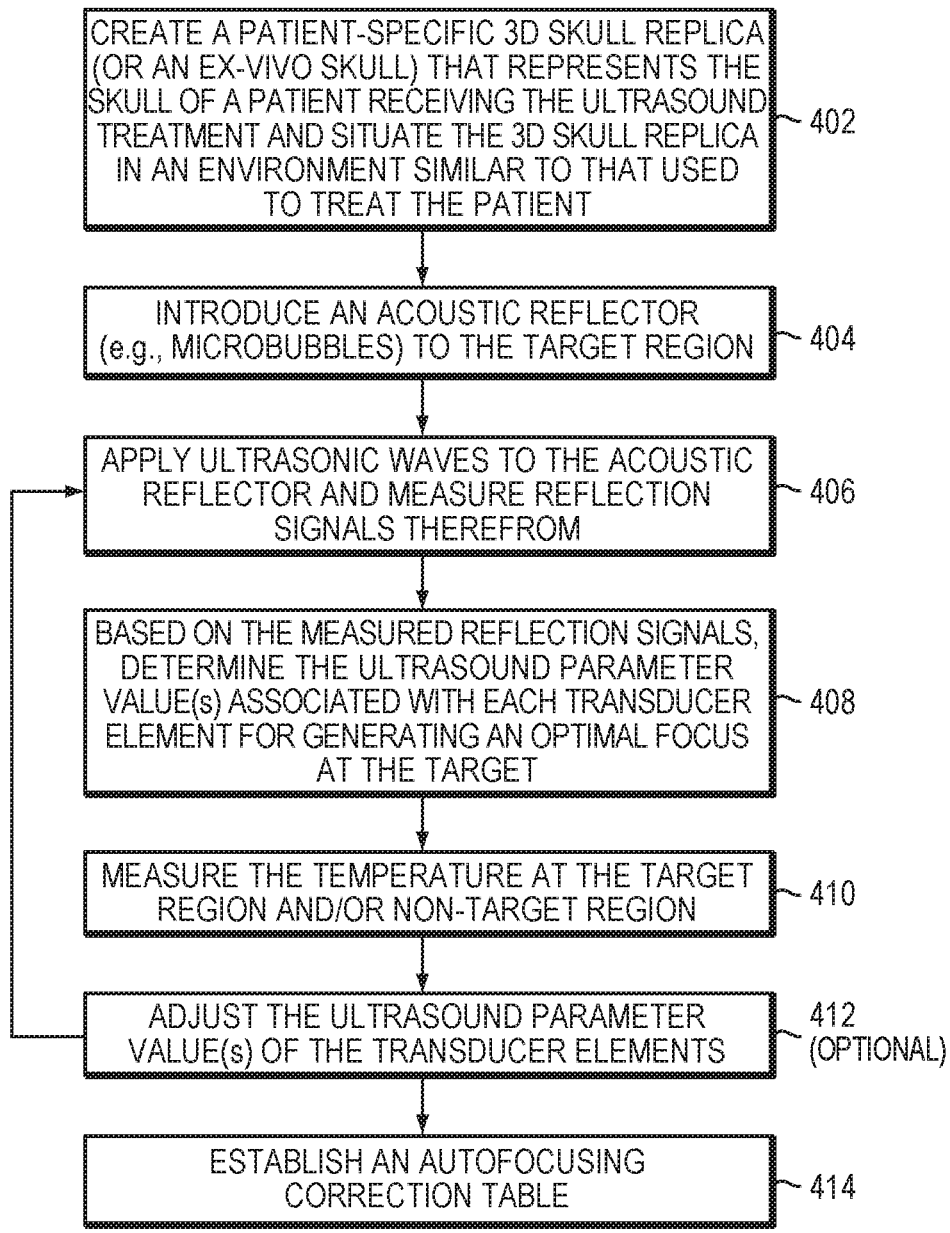
FIG. 4A-4C are flow charts illustrating exemplary approaches for establishing an autofocusing correction table in accordance with various embodiments of the present invention.
Figure 4B:
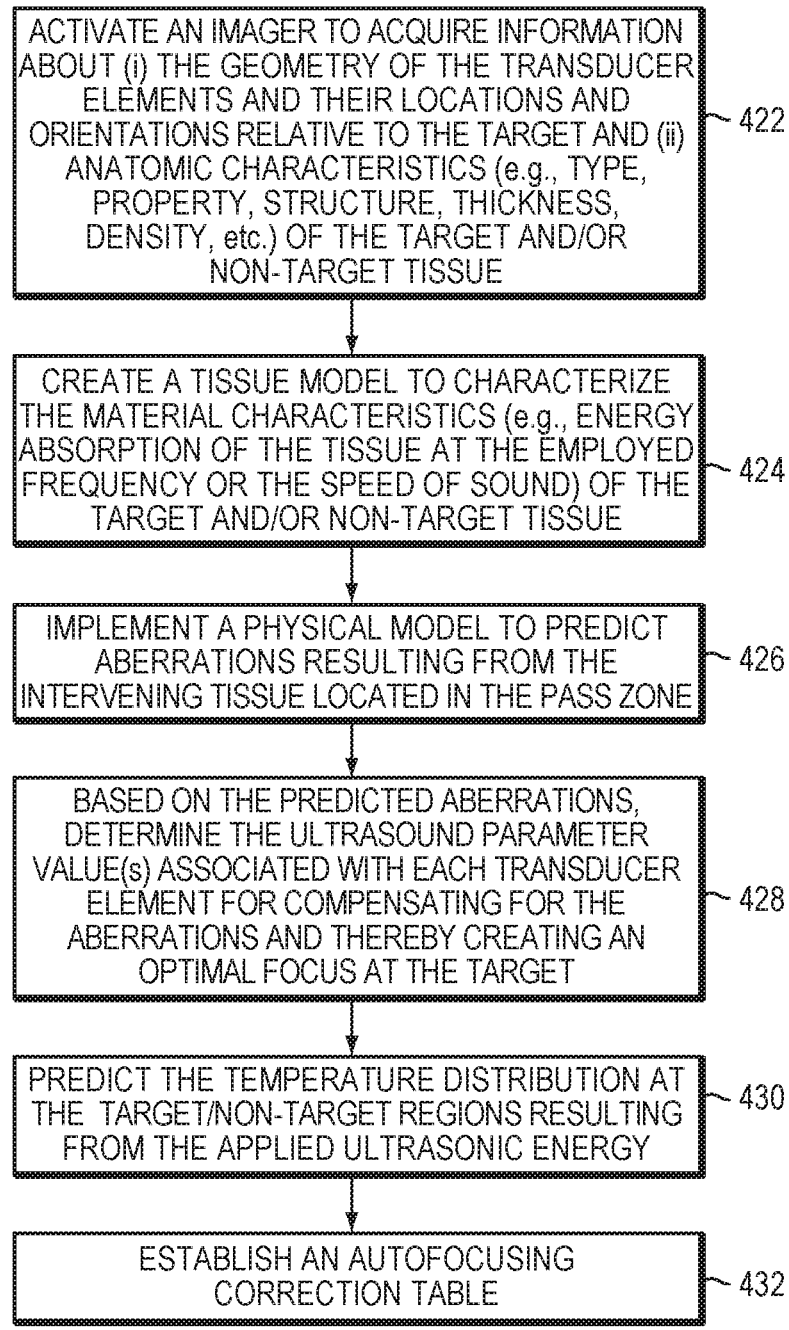
Figure 4C:
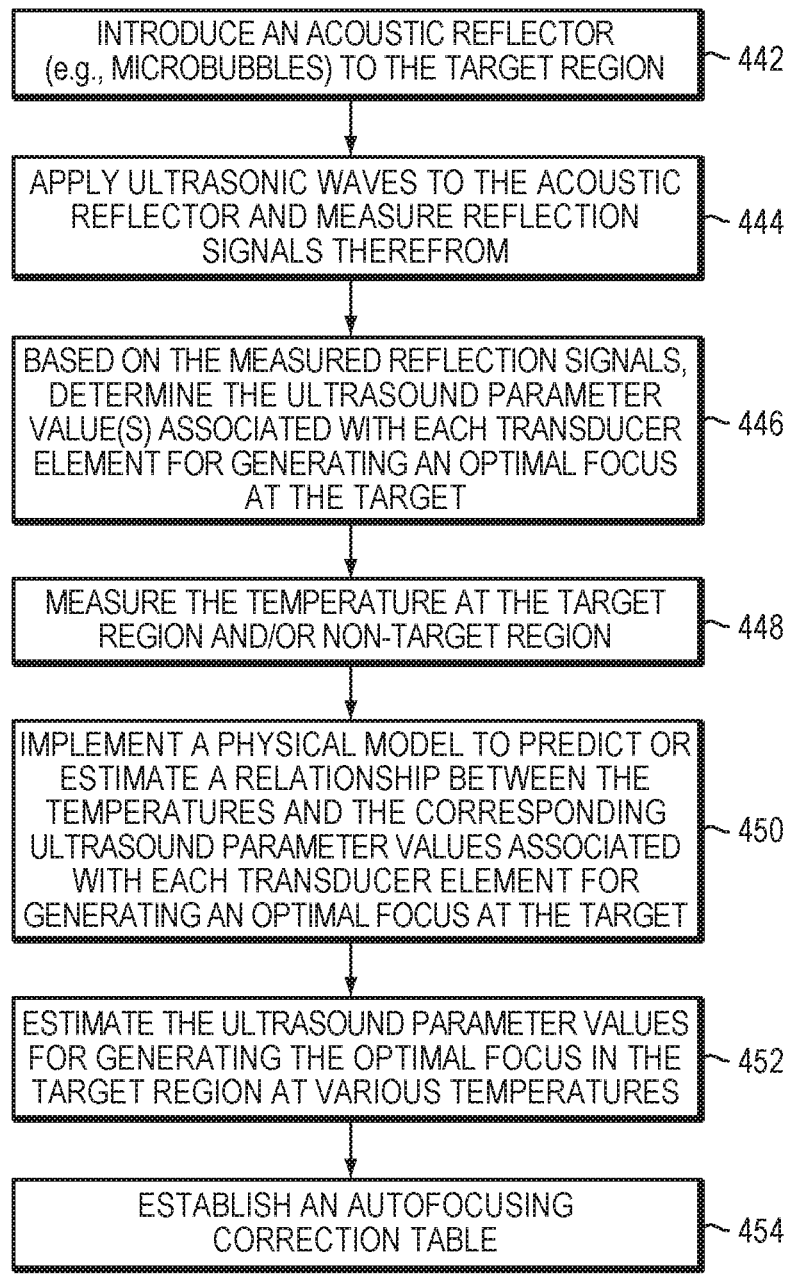

FIGS. 4A-4C are flow charts illustrating exemplary approaches for establishing an autofocusing correction table in accordance herewith. The autofocusing correction table may be established based on measurements, predictions or a combination thereof. For example, referring to FIG. 4A, in a first step 402, prior to the ultrasound treatment procedure, a patient-specific 3D skull replica (or an ex-vivo skull) that represents the skull of the patient receiving the ultrasound treatment may be created and situated in an environment similar to that used to treat the patient. In a second step 404, an acoustic reflector (e.g., microbubbles) can be introduced (e.g., generated by applying acoustic energy using the transducer 102 and/or introduced by systemic injection using the administration system 126) to the target region. In a third step 406, the transducer 102 is activated to apply ultrasonic waves to the acoustic reflector and measure reflection signals therefrom. In a fourth step 408, the ultrasound parameter value(s) associated with each transducer element 104 for generating an optimal focus at the target can be determined based on the measured reflection signals. In a fifth step 410, the temperature at the target region and/or non-target region resulting from application of the ultrasonic waves is measured using, for example, the imager 112. Optionally, the ultrasound parameter value(s) of the transducer elements 104 may be adjusted (step 412); steps 406-412 may be iteratively performed. Subsequently, the autofocusing correction table relating the temperatures to the ultrasound parameter value(s) for creating an optimal focus (or achieving another additional objective besides reaching the desired therapeutic temperature) at the target can be established (step 414).

FIG. 4B depicts an approach for establishing the autofocusing correction table prior to performing the ultrasound treatment procedure using a physical model. In a first step 422, the imager 112 is activated to acquire information such as (i) the geometry of the transducer elements and their locations and orientations relative to the target and/or (ii) anatomic characteristics (e.g., type, property, structure, thickness, density, etc.) of the target and/or non-target tissue. In a second step 424, a tissue model characterizing the material characteristics (e.g., energy absorption of the tissue at the employed frequency or the speed of sound) of the target and/or non-target tissue is established based on the information acquired in step 422. In a third step 426, a physical model is implemented to predict aberrations caused by the intervening tissue located in the pass zone based on the information acquired in step 422 and the tissue model established in step 424. In a fourth step 428, the ultrasound parameter value(s) associated with each transducer element 104 for compensating for the aberrations and creating an optimal focus at the target can be determined based on the predicted aberrations. In a fifth step 430, the physical model predicts the temperature distribution at the target/non-target regions resulting from the applied ultrasonic energy. In a sixth step 432, the autofocusing correction table relating the temperatures to the ultrasound parameter value(s) for creating an optimal focus (or achieving another additional objective besides reaching the desired therapeutic temperature) at the target is established.

FIG. 4C depicts an approach for establishing the autofocusing correction table during the ultrasound treatment procedure. In a first step 442, an acoustic reflector (e.g., microbubbles) is introduced to the target region 101. In a second step 444, the transducer 102 is activated to apply ultrasonic waves to the acoustic reflector and measure reflection signals therefrom. In a third step 446, the ultrasound parameter value(s) associated with each transducer element 104 for generating an optimal focus at the target can be determined based on the measured reflection signals. In a fourth step 448, the temperature at the target region and/or non-target region is measured using, for example, the imager 112. In a fifth step 450, the physical model is implemented to predict or estimate a relationship between the temperatures and the corresponding ultrasound parameter values associated with each transducer element for generating an optimal focus at the target. In addition, the physical model may estimate the ultrasound parameter values for generating the optimal focus in the target region at various temperatures (step 452). The autofocusing correction table relating the temperatures to the ultrasound parameter value(s) for creating an optimal focus at the target is then established (step 454).

Figure 5:
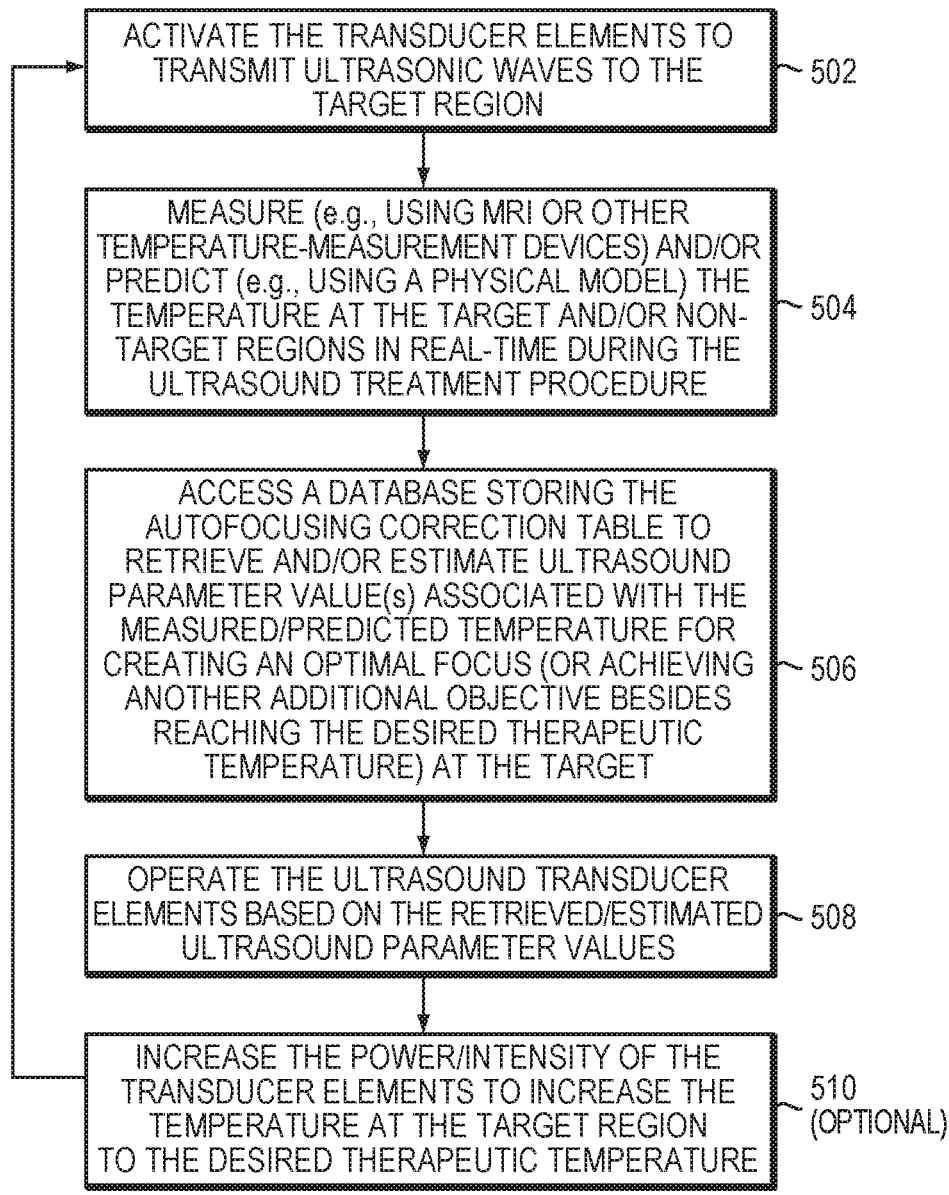
FIG. 5 is a flow chart illustrating an exemplary ultrasound treatment procedure in accordance with various embodiments of the present invention.

FIG. 5 is a flow chart illustrating an approach for performing an ultrasound treatment procedure in accordance herewith. In a first step 502, the transducer 102 is activated to transmit ultrasound waves to the target region 101; in one embodiment, application of the ultrasound waves results in a temperature increase at the target and/or non-target region that is less than a predetermined threshold (e.g., without causing a significant clinical effect). In a second step 504, the temperature at the target and/or non-target regions is measured (e.g., using MRI or other temperature-measurement devices) and/or predicted (e.g., using a physical model) in real time during the ultrasound treatment procedure. In a third step 506, the controller 108 associated with the transducer 102 accesses a database storing the autofocusing correction table to retrieve and/or estimate the ultrasound parameter value(s) for creating an optimal focus (or achieving another additional objective besides reaching the desired therapeutic temperature) at the target based on the measured/predicted temperature. In a fourth step 508, the ultrasound transducer elements are operated based on the retrieved/estimated ultrasound parameter value(s). In an optional fifth step 510, the power/intensity of the transducer elements may be adjusted to increase the temperature at the target region for treatment thereof. Steps 502-510 may be iteratively performed until the desired therapeutic temperature at the target 101 is reached.

It should be noted that the target region to which the ultrasound waves are applied for establishing the autofocusing correction table 202 may be the same or different from the target region to which the ultrasound waves are applied for treatment. For example, referring again to FIG. 3A, the target region may include multiple portions 302-308; the ultrasound waves may be first transmitted to the portion 302 for establishing the autofocusing correction table 202 as described above. Once the autofocusing correction table 202 is established, the transducer elements 104 may transmit ultrasound waves to the portion 302 or a different portion (e.g., portion 304, 306, 308) for necrosis of the tissue therein as described above. Again, the ultrasound parameter values for necrosis of the tissue in the portion different from the portion 302 may be interpolated or extrapolated based on the data associated with the portion 302 in the autofocusing correction table 202.

Accordingly, various embodiments advantageously improve the treatment efficiency of the target by accounting for the effects (e.g., defocusing, mismatching of the acoustic coupling, etc.) on the target/non-target tissue resulting from acoustic energy application during the ultrasound procedure and, based thereon, adjusting the ultrasound parameter value (s) to achieve an additional objective (e.g., optimal focusing, matching of the acoustic coupling, etc.) prior to adjusting the ultrasound parameter value(s) for achieving the desired therapeutic temperature. As a result, the acoustic energy and intensity may be sufficiently generated in the focus for treatment purposes while damage to the non-target tissue located in the path zones can be avoided (or at least reduced).

In general, functionality for performing an ultrasound treatment procedure, including, for example, creating a patient-specific 3D skull replica (or an ex-vivo skull) that represents the skull of a patient receiving the ultrasound treatment, operating an imager to acquire information about (i) the geometry of the transducer elements and their locations and orientations relative to the target and (ii) anatomic characteristics (e.g., type, property, structure, thickness, density, etc.) of the target and/or non-target tissue, creating a tissue model to characterize the material characteristics of the target and/or non-target tissue, implementing a physical model to predict aberrations resulting from the intervening tissue located in the pass zone and the temperature distribution at the target/non-target regions resulting from application of the ultrasonic energy, introducing an acoustic reflector (e.g., microbubbles) to the target region, applying ultrasound waves to the acoustic reflector and measuring reflection signals therefrom, measuring and/or predicting the temperatures at the target/non-target regions, determining the ultrasound parameter value(s) associated with each transducer element for generating an optimal focus at the target, establishing the autofocusing correction table, storing the autofocusing correction table in a database, accessing the database to retrieve data stored therein, and dynamically adjusting the ultrasound parameter values (e.g., frequencies, amplitudes, phases, etc.) prior to and/or during the ultrasound treatment procedure, as described above, whether integrated within a controller of the imager, and/or an ultrasound system, or provided by a separate external controller, may be structured in one or more modules implemented in hardware, software, or a combination of both. For embodiments in which the functions are provided as one or more software programs, the programs may be written in any of a number of high level languages such as PYTHON, JAVA, C, C++, C#, BASIC, various scripting languages, and/or HTML. Additionally, the software can be implemented in an assembly language directed to the microprocessor resident on a target computer (e.g., the controller); for example, the software may be implemented in Intel 80×86 assembly language if it is configured to run on an IBM PC or PC clone. The software may be embodied on an article of manufacture including, but not limited to, a floppy disk, a jump drive, a hard disk, an optical disk, a magnetic tape, a PROM, an EPROM, EEPROM, field-programmable gate array, or CD-ROM. Embodiments using hardware circuitry may be implemented using, for example, one or more FPGA, CPLD or ASIC processors.

In addition, the term "controller" used herein broadly includes all necessary hardware components and/or software modules utilized to perform any functionality as described above; the controller may include multiple hardware components and/or software modules and the functionality can be spread among different components and/or modules.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A system for delivering ultrasound energy to a target region during treatment thereof, the system comprising:
    an ultrasound transducer comprising a plurality of transducer elements; and
    a controller configured to:
    (a) prior to the treatment, populate a data structure relating a plurality of real-time parameter values to corresponding correction values for at least one ultrasound parameter value associated with at least one transducer element for generating a focal zone of acoustic energy in at least a first portion of the target region; and
    (b) during the treatment:
        (i) predict or cause measurement of at least one of the real-time parameter values in a second portion of the target region or a non-target region;
        (ii) based at least in part on the predicted or measured real-time parameter value and contents of the data structure, determine the correction value for the at least one ultrasound parameter value; and
        (iii) activate the at least one transducer element based at least in part on the determined correction value so as to generate the focal zone in the second portion of the target region.

2. The system of claim 1, wherein each of the real-time parameter values in the data structure represents a change in a value of an associated real-time parameter.

3. The system of claim 2, wherein the associated real-time parameter comprises at least one of a temperature, a change in tissue perfusion, a number of cavitation events, an accumulated energy absorbed in the target and/or non-target regions, a number of sonications, a time interval between sonications, a contrast in magnetic resonance imaging (MRI) image, a temperature profile as a function of time, or an amplitude and/or a phase associated with an acoustic signal reflected from intervening tissue located between the ultrasound transducer and the target region.

4. The system of claim 1, wherein the data structure comprises a plurality of ranges of the real-time parameter values, each range corresponding to one of the correction values for the at least one ultrasound parameter value, the controller being further configured to:
    identify the range of the real-time parameter values to which the predicted or measured real-time parameter value belongs; and
    based thereon, determine the correction value for the at least one ultrasound parameter.

5. The system of claim 1, wherein the data structure comprises a plurality of ranges of the real-time parameter values, each range corresponding to a range of the correction values for the at least one ultrasound parameter value, the controller being further configured to:
    identify the range of the real-time parameter values in the data structure to which the predicted or measured real-time parameter value belongs;
    based thereon, determine the corresponding range of the correction values; and
    determine the correction value for the at least one ultrasound parameter value in the range of the correction values based at least in part on where within the identified range the predicted or measured real-time parameter value occurs.

6. The system of claim 1, further comprising at least one of an imager or a temperature-measurement device for measuring the at least one of the real-time parameter values at the second portion of the target region or the non-target region.

7. The system of claim 1, wherein the controller is further configured to predict the at least one of the real-time parameter values at the second portion of the target region or the non-target region using a physical model.

8. The system of claim 1, wherein the ultrasound parameter value comprises at least one of a frequency, a phase or a power level.

9. The system of claim 8, wherein the controller is further configured to adjust the power level associated with the at least one transducer element so as to achieve a target temperature in the second portion of the target region.

10. The system of claim 1, wherein the controller is further configured to repeat steps (i)-(iii) during the treatment.

11. The system of claim 1, wherein the plurality of real-time parameter values in the data structure do not include the predicted or measured real-time parameter value, the controller being further configured to determine the correction value for the at least one ultrasound parameter value using an interpolation or an extrapolation based on the plurality of real-time parameter values and the corresponding correction values for the at least one ultrasound parameter value in the data structure.

12. The system of claim 1, wherein the plurality of real-time parameter values in the data structure comprise combinations of the parameter values measured in real-time and the parameter values computed using a physical model.

13. The system of claim 1, wherein the first portion and the second portion of the target region are the same.

14. The system of claim 1, wherein the first portion of the target region is different from the second portion of the target region.

15. The system of claim 14, wherein the controller is further configured to determine the correction value for the at least one ultrasound parameter value using an interpolation or an extrapolation based on the plurality of real-time parameter values in the data structure and the corresponding correction values for the at least one ultrasound parameter value for generating the focal zone in the first portion of the target region.

16. The system of claim 1, wherein the controller is further configured to:
determine an acoustic energy delivered to the focal zone by the at least one transducer element after traversing an intervening tissue region; and
adjust a power level associated with the at least one transducer element based at least in part on the delivered acoustic energy.

17. The system of claim 16, wherein the controller is further configured to reduce the power level of the at least one transducer element when the delivered acoustic energy in the focal zone is below a predetermined threshold.

18. The system of claim 16, wherein the controller is further configured to increase the power level of the at least one transducer element when the delivered acoustic energy in the focal zone exceeds a predetermined threshold.

19. The system of claim 1, wherein the controller is further configured to predict or cause measurement of a distribution of the at least one of the real-time parameter values in the second portion of the target region or the non-target region, wherein the correction value for the at least one ultrasound parameter value is further determined based on the predicted or measured distribution of the at least one of the real-time parameter values.

20. A method of operating a system for delivering ultrasound energy to a target region during treatment thereof, the system comprising an ultrasound transducer comprising a plurality of transducer elements and a controller, the method comprising:
(a) prior to the treatment, populating a data structure relating a plurality of real-time parameter values to corresponding correction values for at least one ultrasound parameter value associated with at least one transducer element for generating a focal zone of acoustic energy in at least a first portion of the target region; and
(b) during the treatment:
(i) predicting or causing measurement of at least one of the real-time parameter values in a second portion of the target region or a non-target region;
(ii) based at least in part on the predicted or measured real-time parameter value and contents of the data structure, determining the correction value for the at least one ultrasound parameter value; and
(iii) activating the at least one transducer element based at least in part on the determined correction value so as to generate the focal zone in the second portion of the target region.

21. The method of claim 20, wherein each of the real-time parameter values in the data structure represents a change in a value of an associated real-time parameter.

22. The method of claim 21, wherein the associated real-time parameter comprises at least one of a temperature, a change in tissue perfusion, a number of cavitation events, an accumulated energy absorbed in the target and/or non-target regions, a number of sonications, a time interval between sonications, a contrast in magnetic resonance imaging (MRI) image, a temperature profile as a function of time, or an amplitude and/or a phase associated with an acoustic signal reflected from intervening tissue located between the ultrasound transducer and the target region.

23. The method of claim 20, wherein the data structure comprises a plurality of ranges of the real-time parameter values, each range corresponding to one of the correction values for the at least one ultrasound parameter value, the method further comprising:
identifying the range of the real-time parameter values to which the predicted or measured real-time parameter value belongs; and
based thereon, determining the correction value for the at least one ultrasound parameter.

24. The method of claim 20, wherein the data structure comprises a plurality of ranges of the real-time parameter values, each range corresponding to a range of the correction values for the at least one ultrasound parameter value, the method further comprising:
identifying the range of the real-time parameter values in the data structure to which the predicted or measured real-time parameter value belongs;
based thereon, determining the corresponding range of the correction values; and
determining the correction value for the at least one ultrasound parameter value in the range of the correction values based at least in part on where within the identified range the predicted or measured real-time parameter value occurs.

25. The method of claim 20, wherein the at least one of the real-time parameter values at the second portion of the target region or the non-target region is predicted using a physical model.

26. The method of claim 20, wherein the ultrasound parameter value comprises at least one of a frequency, a phase or a power level.

27. The method of claim 26, further comprising adjusting the power level associated with the at least one transducer element so as to achieve a target temperature in the second portion of the target region.

28. The method of claim 20, further comprising repeating steps steps (i)-(iii) during the treatment.

29. The method of claim 20, wherein the plurality of real-time parameter values in the data structure do not include the predicted or measured real-time parameter value, the method further comprising computationally determining the correction value for the at least one ultrasound parameter value using an interpolation or an extrapolation based on the plurality of real-time parameter values and the corresponding correction values for the at least one ultrasound parameter value in the data structure.

30. The method of claim 20, wherein the first portion and the second portion of the target region are the same.

31. The method of claim 20, wherein the first portion of the target region is different from the second portion of the target region.

32. The method of claim 31, further comprising computationally determining the correction value for the at least one ultrasound parameter value using an interpolation or an extrapolation based on the plurality of real-time parameter values in the data structure and the corresponding correction values for the at least one ultrasound parameter value for generating the focal zone in the first portion of the target region.

33. The method of claim 20, further comprising predicting or causing measurement of a distribution of the at least one of the real-time parameter values in the second portion of the target region or the non-target region, wherein the correction value for the at least one ultrasound parameter value is further determined based on the predicted or measured distribution of the at least one of the real-time parameter values.

\* \* \* \* \*